(12) United States Patent
Ogiwara et al.

(10) Patent No.: US 8,024,155 B2
(45) Date of Patent: Sep. 20, 2011

(54) SAMPLE DATA RELIABILITY EVALUATION METHOD AND SAMPLE DATA RELIABILITY EVALUATION APPARATUS

(75) Inventors: Shinya Ogiwara, Hino (JP); Tetsuya Tanabe, Shibuya (JP)

(73) Assignee: Olympus Corporation, Tokyo (JP)

( * ) Notice: Subject to any disclaimer, the term of this patent is extended or adjusted under 35 U.S.C. 154(b) by 201 days.

(21) Appl. No.: 12/403,923

(22) Filed: Mar. 13, 2009

(65) Prior Publication Data

US 2009/0187376 A1    Jul. 23, 2009

Related U.S. Application Data

(63) Continuation of application No. PCT/JP2007/067946, filed on Sep. 14, 2007.

(51) Int. Cl.
*G06F 15/00* (2006.01)

(52) U.S. Cl. ...................................... 702/189

(58) Field of Classification Search .................. 702/189, 702/179, 158
See application file for complete search history.

(56) References Cited

U.S. PATENT DOCUMENTS

| | | | |
|---|---|---|---|
| 2003/0067998 A1* | 4/2003 | Nakajima et al. | 375/341 |
| 2004/0126782 A1 | 7/2004 | Holden et al. | |

FOREIGN PATENT DOCUMENTS

| | | |
|---|---|---|
| JP | 2003-28855 A | 1/2003 |
| JP | 2005-257660 A | 9/2005 |
| JP | 2005-275556 A | 10/2005 |
| JP | 2005-531853 A | 10/2005 |
| JP | 2006-163894 A | 6/2006 |

OTHER PUBLICATIONS

K. L. Gunderson "A genome-wide scalable SNP genotyping assay using microarray technology," Nature Genetics; 2005; vol. 37; pp. 549-554.
International Search Report of PCT/JP2007/067946, date of mailing Nov. 20, 2007.

* cited by examiner

*Primary Examiner* — Bryan Bui
(74) *Attorney, Agent, or Firm* — Westerman, Hattori, Daniels & Adrian, LLP

(57) ABSTRACT

A sample data reliability evaluation method includes a first calculating step of calculating a representative distance between samples of a same cluster, which is a representative distance between the sample and the sample belonging to the same cluster to that to which the sample belongs, a second calculating step of calculating a representative distance between samples of different clusters, which is a representative distance between the sample and the sample belonging to the different cluster from that to which the sample belongs, a third calculating step of calculating a reliability evaluation index, which is an index for evaluating reliability of the sample data based on the representative distance between samples of the same cluster and the representative distance between samples of different clusters, and an evaluating step of evaluating the reliability of a subset of the sample data set or the whole sample data set.

8 Claims, 8 Drawing Sheets

| SAMPLE ID | CLUSTER ID | SIGNAL DATA |
|---|---|---|
| $S_1$ | $C_1$ | $(S_{11}, S_{12}, \cdots, S_{1p}, \cdots, S_{1P})$ |
| $\vdots$ | $\vdots$ | $\vdots$ |
| $S_m$ | $C_n$ | $(S_{m1}, S_{m2}, \cdots, S_{mp}, \cdots, S_{mP})$ |
| $\vdots$ | $\vdots$ | $\vdots$ |
| $S_M$ | $C_N$ | $(S_{M1}, S_{M2}, \cdots, S_{Mp}, \cdots, S_{MP})$ |

| SAMPLE ID | REPRESENTATIVE DISTANCE BETWEEN SAMPLE OF THE SAME CLUSTER | REPRESENTATIVE DISTANCE BETWEEN SAMPLE OF DIFFERENT CLUSTER | SAMPLE RELIABILITY EVALUATION INDEX |
|---|---|---|---|
|  |  |  |  |
| $\vdots$ | $\vdots$ | $\vdots$ | $\vdots$ |

SAMPLE DATA RELIABILITY EVALUATION METHOD AND SAMPLE DATA RELIABILITY EVALUATION APPARATUS

BACKGROUND OF THE INVENTION

1. Field of the Invention

The present invention relates to an evaluation of reliability of sample data to classify samples and quality control of sample data.

2. Description of the Related Art

In a polymorphic analysis of samples derived from a living body, the rate of progress of a polymorphic identification reaction is different from sample to sample depending on concentrations of the sample and presence/absence of inhibitors. Thus, polymorphic data having a wide distribution is obtained from polymorphic analysis.

Conventionally, the polymorphic analysis has been performed by using a statistical technique or genetic technique on signals of sample.

However, particularly for polymorphic analysis concerning genetic polymorphism, there are some kinds of polymorphism that are present only in several samples among several hundreds of samples, and thus statistics based on the conventional statistical technique may be meaningless.

Therefore, for polymorphic analysis concerning genetic polymorphism, reliability of polymorphic data obtained by the polymorphic analysis is generally evaluated genetic-statistically by using the Hardy-Weinberg equilibrium. Also, Kevin L Gunderson, Frank J Steemers, Grace Lee, Leo G Mendoza, and Mark S Chee, "A genome-wide scalable SNP genotyping assay using microarray technology", NATURE GENETICS, VOLUME37, NUMBER 5, MAY, 2005 is disclosed as a technology to evaluate reliability of polymorphic data obtained by polymorphic analysis concerning genetic polymorphism. More specifically, the evaluation index "CSS" disclosed by Kevin L Gunderson, Frank J Steemers, Grace Lee, Leo G Mendoza, and Mark S Chee, "A genome-wide scalable SNP genotyping assay using microarray technology", NATURE GENETICS, VOLUME37, NUMBER5, MAY, 2005, uses statistics for each cluster.

Figure 10:
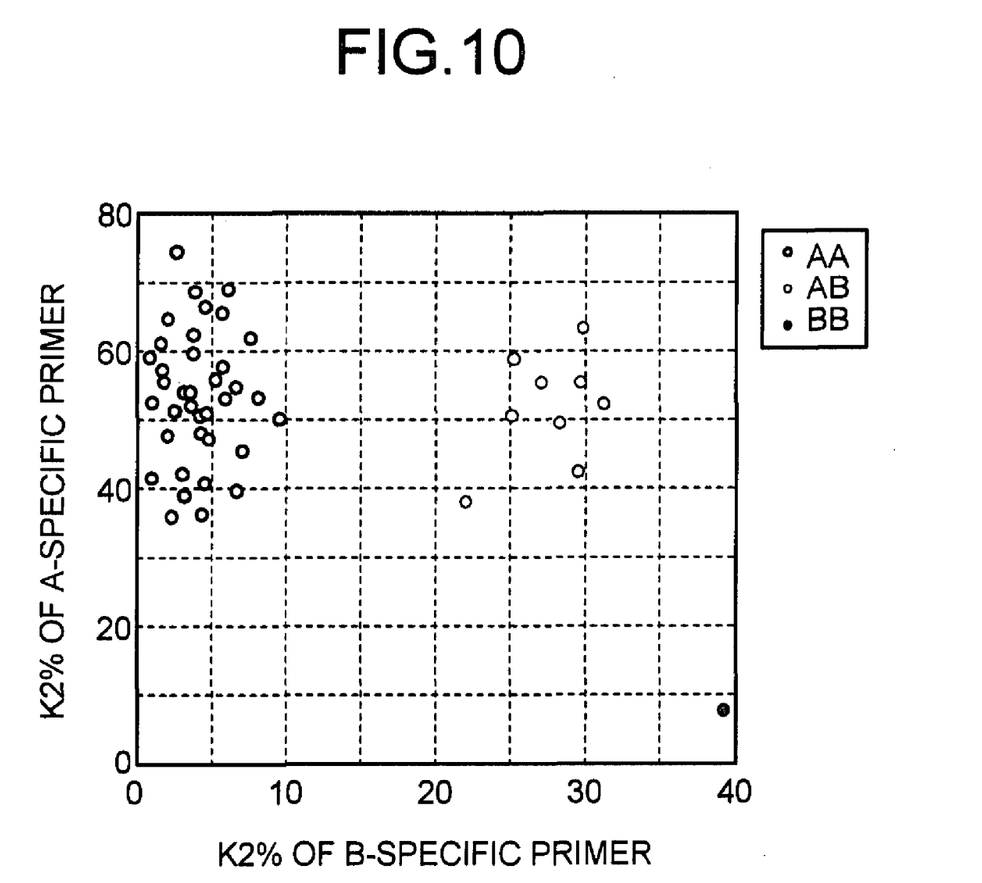
FIG. 10 is a diagram exemplifying polymorphic data whose frequency is small, which is difficult to evaluate by conventional technology.

However, these conventional evaluation techniques assume that polymorphic data obtained from samples sampled from a group of random crossing is evaluated, and thus, for example, polymorphic data obtained from samples sampled only from specific samples such as family samples and patient samples are not appropriate for evaluation. If, for example, polymorphic data having only one genotype "BB" shown in FIG. 10 is selected for evaluation, no distribution/average corresponding to clusters of genotype "BB" is obtained, and thus it is difficult to calculate an evaluation value by the above conventional evaluation techniques.

That is, when a group is not obtained from random crossing or polymorphic data containing polymorphism whose frequency is small is obtained from polymorphic analysis concerning genetic polymorphism, it is difficult to evaluate reliability of such polymorphic data by the conventional evaluation technique.

Thus, conventionally, skilled operators have subjectively evaluated reliability of polymorphic data containing polymorphism whose frequency is small to extract error samples or decide the threshold of type classification.

SUMMARY OF THE INVENTION

The sample data reliability evaluation method according to one aspect of the present invention includes a first calculating step of calculating a representative distance between samples of a same cluster, which is a representative distance between the sample and the sample belonging to the same cluster to that to which the sample belongs, based on a sample data set having a plurality of pieces of sample data concerning clustered samples as elements, a second calculating step of calculating a representative distance between samples of different clusters, which is a representative distance between the sample and the sample belonging to the different cluster from that to which the sample belongs based on the sample data set, a third calculating step of calculating a reliability evaluation index, which is an index for evaluating reliability of the sample data based on the representative distance between samples of the same cluster calculated at the first calculating step and the representative distance between samples of different clusters calculated at the second calculating step, and an evaluating step of evaluating the reliability of a subset of the sample data set or the whole sample data set based on the reliability evaluation index calculated at the third calculating step.

The sample data reliability evaluation apparatus according to one aspect of the present invention includes a first calculator that calculates a representative distance between samples of a same cluster, which is a representative distance between the sample and the sample belonging to the same cluster to that to which the sample belongs, based on a sample data set having a plurality of pieces of sample data concerning clustered samples as elements, a second calculator that calculates a representative distance between samples of different clusters, which is a representative distance between the sample and the sample belonging to the different cluster from that to which the sample belongs based on the sample data set, a third calculator that calculates a reliability evaluation index, which is an index for evaluating reliability of the sample data based on the representative distance between samples of the same cluster calculated by the first calculator and the representative distance between samples of different clusters calculated by the second calculator, and an evaluator that evaluates the reliability of a subset of the sample data set or the whole sample data set based on the reliability evaluation index calculated by the third calculator.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a diagram exemplifying information stored in a sample data set file 106a.

DETAILED DESCRIPTION OF THE PREFERRED EMBODIMENTS

The following describes an embodiment of a sample data reliability evaluation method, and a sample data reliability evaluation apparatus according to the present invention in detail with reference to the drawings. The embodiment is illustrative only, and is not intended to limit the present invention in any way. The following outlines the present invention, and then, a configuration and processing of the present invention are explained in detail.

Overview of the Invention

Figure 1:
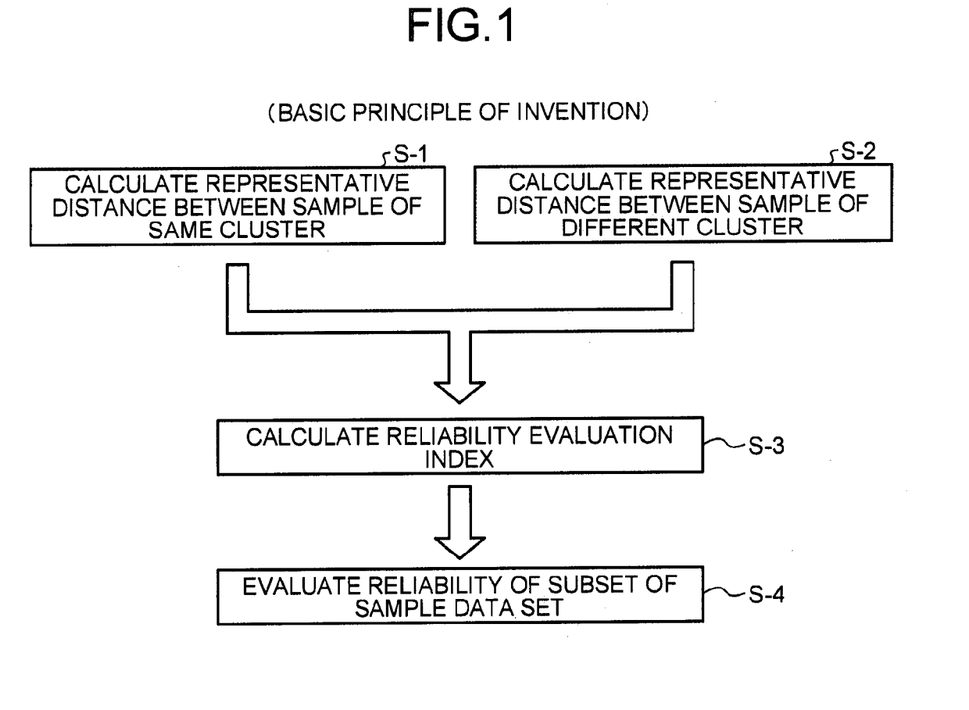
FIG. 1 is a schematic diagram of principle showing a basic principle of the present invention.

The following outlines the present invention with reference to FIG. 1. FIG. 1 is a schematic diagram of principle showing a basic principle of the present invention. In general, the invention has schematically following basic features.

In the present invention, a representative distance between samples of the same cluster and that between samples of different clusters are first calculated based on a sample data set, which is a set having a plurality of pieces of sample data concerning clustered samples as elements, for each piece of sample data (step S-1 and step S-2). The representative distance between samples of the same cluster is a representative distance between a certain sample and another sample belonging to the same cluster as the certain sample. The representative distance between samples of different clusters is a representative distance between a certain sample and another sample belonging to a different cluster from that of the certain sample.

Next, in the present invention, the reliability evaluation index (for example, the sample reliability evaluation index, which is an index for evaluating reliability of sample data and an average value of the sample reliability evaluation index), which is an index to valuate reliability of a sample data subset, which is a subset of the sample data set, is calculated based on at least one pair of the representative distance between samples of the same cluster calculated at step S-1 and the representative distance between samples of different clusters calculated at step S-2 for each sample data subset (step S-3).

Here, an average distance between samples of the same cluster, which is an average distance between a certain sample and another sample belonging to the same cluster as the certain sample, may be calculated as the representative distance between samples of the same cluster at step S-1, a minimum distance between samples of different clusters, which is a minimum distance between a certain sample and another sample belonging to a different cluster from that of the certain sample, as the representative distance between samples of different clusters at step S-2, and a ratio of the average distance between samples of the same cluster to the minimum distance between samples of different clusters or an average of the ratio as the reliability evaluation index at step S-3. Accordingly, an effect of being able to obtain an evaluation value for each sample is achieved.

Next, in the present invention, reliability of the sample data subset is evaluated based on at least one reliability evaluation index calculated at step S-3 for each sample data subset (step S-4). Here, a sample data subset with lower reliability may be extracted or reliability of the algorithm used for clustering may be evaluated at step S-4. Accordingly, an effect of being able to improve the algorithm, setting criteria dynamically, or extracting an error sample is obtained.

An overview of the present invention is provided above, and the representative distance between samples of the same cluster and the representative distance between samples of different clusters may be based on the Euclid distance, standardized Euclid distance, Minkowski distance, or Mahalanobis distance. Accordingly, an effect of being able to calculate the representative distance between samples of the same cluster and the representative distance between samples of different clusters appropriately in accordance with properties of sample data is obtained.

Also, in the present invention, the reliability evaluation index and evaluation results may be output (for example, displaying or printing). Accordingly, subjective clustering by an operator can be supported so that an effect of being able to reduce differences between operators regarding evaluation (judgment) of reliability is obtained.

Also, in the present invention, the representative distance between samples of the same cluster and the representative distance between samples of different clusters may be calculated based on a sample data set in converted polar coordinates after converting each piece of sample data of the sample data set into polar coordinates and defining a difference of angle between samples as a distance. Accordingly, an effect of being able to evaluate reliability when there is a large difference in signal strength in a group of the same type is obtained.

Also, in the present invention, a sample data subset may have one piece of sample data as an element, a plurality of pieces of sample data as elements, or all pieces of sample data as elements (sample data set). Accordingly, the reliability evaluation index can be calculated in units of samples, clusters, or total samples (specifically, in units of experiment); as a result, an effect of being able to evaluate reliability of a sample data subset in units of samples, clusters, or total samples (specifically, in units of experiment) is obtained.

Configuration of the System

Figure 2:
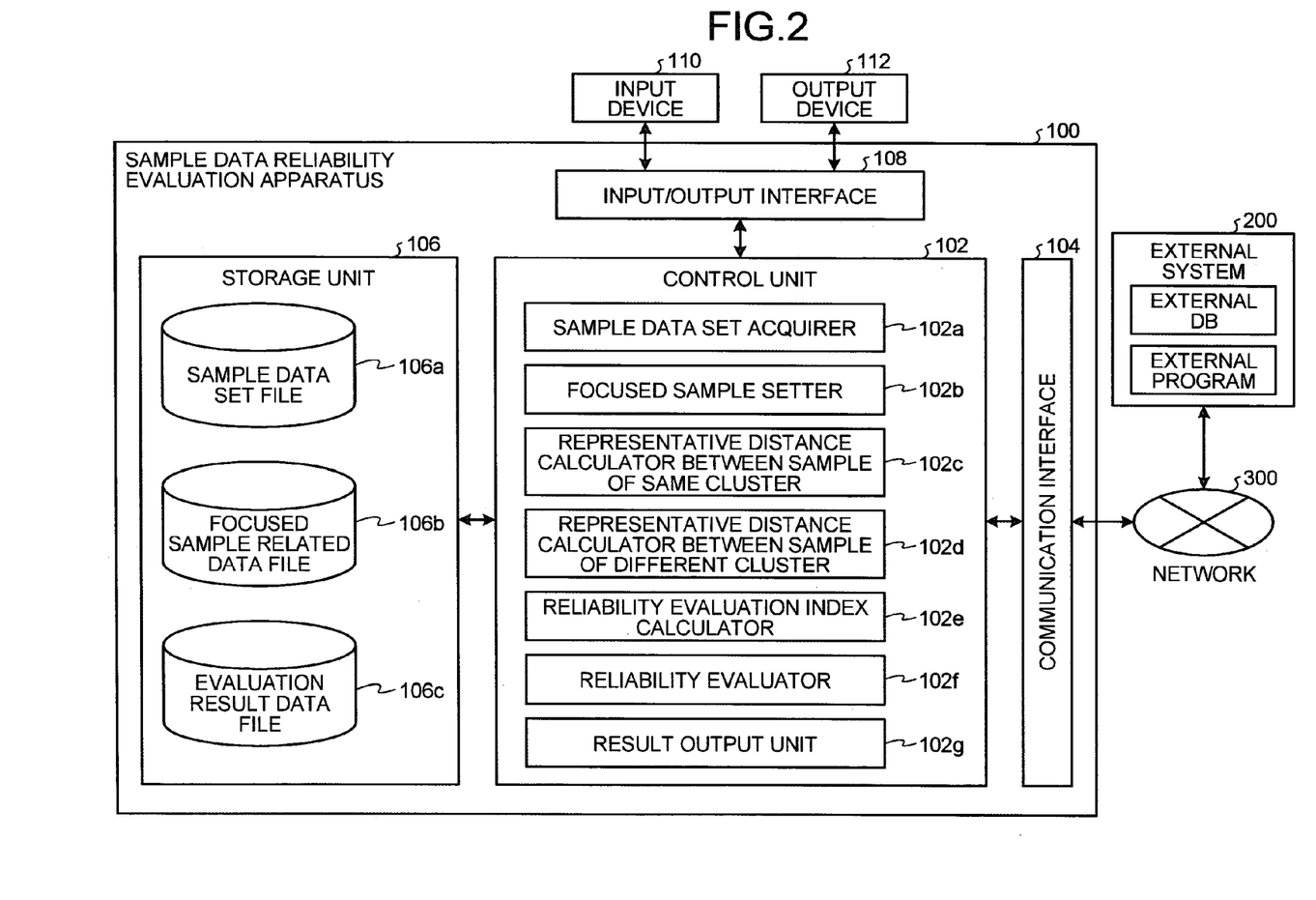
FIG. 2 is a block diagram showing the configuration of a sample data reliability evaluation apparatus 100.
Figure 3:
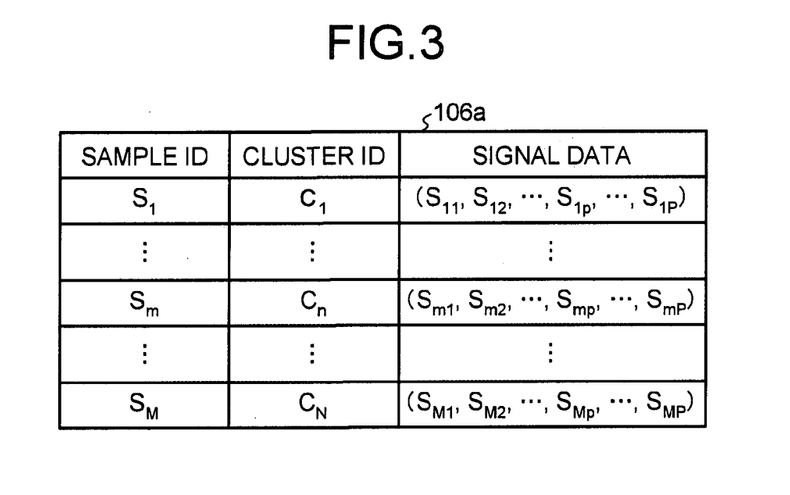
Figure 4:
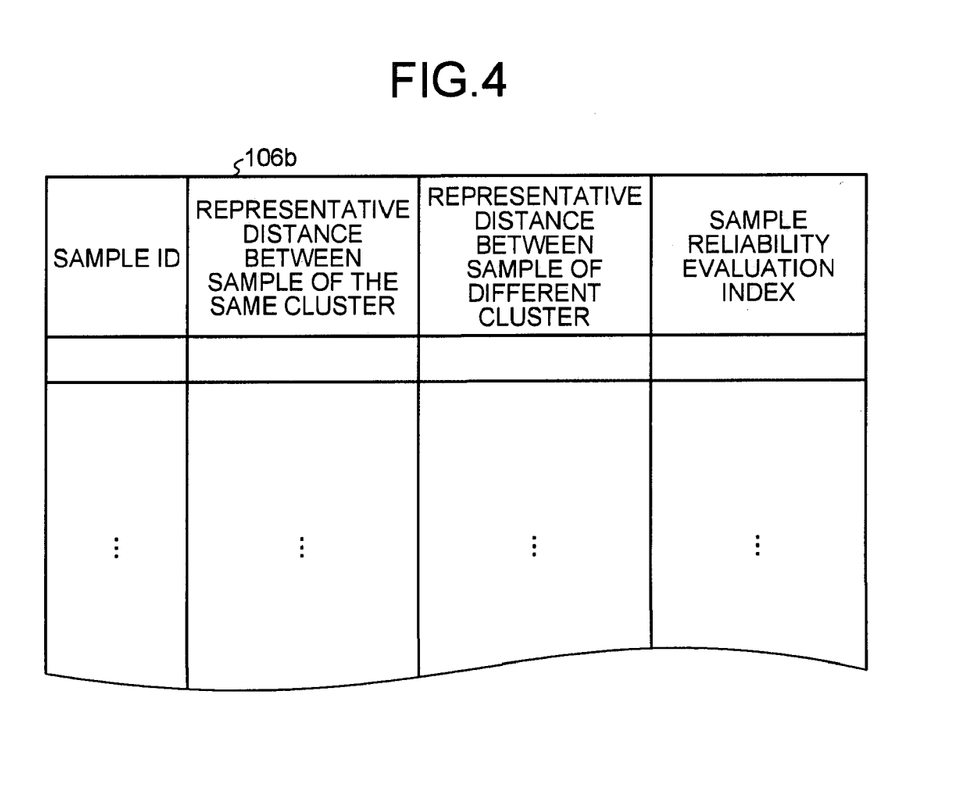
FIG. 4 is a diagram exemplifying information stored in a focused sample related data file 106b.

The following describes a configuration of a sample data reliability evaluation apparatus 100 to which the present embodiment is applied, with reference to FIG. 2 to FIG. 4. FIG. 2 is a block diagram showing the configuration of the sample data reliability evaluation apparatus 100, and conceptually shows only parts related to the present invention.

The sample data reliability evaluation apparatus 100 is provided with a control unit 102 such as a central processing unit (CPU) which controls the sample data reliability evaluation apparatus 100 totally, a communication interface 104 which communicatably connects the sample data reliability evaluation apparatus 100 to a network 300 through a communication device such as a router, and a wired or wireless communication line such as a dedicated line, a storage unit 106 which stores various databases, various tables, various file, and an input/output interface 108 which connects to an input device 110 and an output device 112, and these parts communicatably connect through an arbitrary communication line.

The storage unit 106 is a storage unit such as memory devices such as random access memory (RAM) and read-only memory (ROM), a fixed disk device such as hard disk (HD), flexible disk, and optic disk. The storage unit 106 stores a sample data set file 106a, a focused sample related data file 106b, and an evaluation result data file 106c as the figure. The storage unit 106 stores various files (the sample data set file 106a to the evaluation result data file 106c), and various programs, various tables, various databases, various file for web page and the like used in various processes.

The sample data set file 106a stores a sample data set. Here, an example of information stored in the sample data set file 106a will be described with reference to FIG. 3. FIG. 3 is a diagram exemplifying information stored in the sample data set file 106a. As shown in FIG. 3, the sample data set file 106a stores a sample data set by mutually associating a sample ID for uniquely identifying the sample as sample identification data, a cluster ID for uniquely identifying the cluster (for example, the type of polymorphism) as cluster identification data, and signal data obtained from measurement of the sample.

Returning to FIG. 2, the focused sample related data file 106b stores data related to a focused sample, which is a sample to be focused and set by a focused sample setter 102b described later. Here, an example of information stored in the focused sample related data file 106b will be described with reference to FIG. 4. FIG. 4 is a diagram exemplifying information stored in the focused sample related data file 106b. As shown in FIG. 4, the focused sample related data file 106b stores a focused sample by mutually associating the sample ID corresponding to the focused sample, representative distance between samples of the same cluster, representative distance between samples of different clusters, and sample reliability evaluation index.

Returning to FIG. 2, the evaluation result data file 106c stores data related to an evaluation result by a reliability evaluator 102f described later for each focused sample data set. The focused sample data set corresponds to a sample data subset in the present invention and has at least one piece of focused sample data (sample data corresponding to the focused sample).

The communication interface 104 mediates communication between the sample data reliability evaluation apparatus 100 and the network 300 (the communication device such as a router). That is, the communication interface 104 has a function of transmitting data to other terminals through a communication line.

The input/output 108 interface connects to the input device 110 and the output device 112. The output device 112 corresponds to a display (monitor), a speaker, a printer, and the like. The input device 110 corresponds to a keyboard, a mouse, microphone, and the like.

The control unit 102 has an internal memory that stores a control program such as an operating system (OS), a program defining various procedures, and required data. The control unit 102 performs information processing for executing various processing by the programs or the like. The control unit 102 is provided with a sample data set acquirer 102a, a focused sample setter 102b, a representative distance calculator between sample of same cluster 102c, a representative distance calculator between sample of different cluster 102d, a reliability evaluation index calculator 102e, a reliability evaluator 102f, and a result output unit 102g as the figure.

The sample data set acquirer 102a acquires a sample data set and stores the acquired sample data set in a predetermined storage area of the sample data set file 106a.

The focused sample setter 102b sets a focused sample from among the sample data set acquired by the sample data set acquirer 102a.

The representative distance calculator between sample of same cluster 102c calculates a representative distance between samples of the same cluster (more specifically, a representative distance between the focused sample and another sample belonging to the same cluster as the focused sample) corresponding to the focused sample set by the focused sample setter 102b based on the sample data set acquired by the sample data set acquirer 102a and stores the representative distance between samples of the same cluster in a predetermined storage area of the focused sample related data file 106b.

The representative distance calculator between sample of different cluster 102d calculates a representative distance between samples of different clusters (more specifically, a representative distance between the focused sample and another sample belonging to a different cluster from that of the certain sample) corresponding to the focused sample set by the focused sample setter 102b based on the sample data set acquired by the sample data set acquirer 102a and stores the representative distance between samples of different clusters in a predetermined storage area of the focused sample related data file 106b.

The reliability evaluation index calculator 102e calculates a sample reliability evaluation index as a reliability evaluation index based on at least one pair of the representative distance between samples of the same cluster calculated by the representative distance calculator between sample of same cluster 102c and the representative distance between samples of different clusters calculated by the representative distance calculator between sample of different cluster 102d for each piece of focused sample data and stores at least one calculated sample reliability evaluation index in a predetermined storage area of the focused sample related data file 106b. The reliability evaluation index calculator 102e also calculates an average value of one or more calculated sample reliability evaluation indexes as a reliability evaluation index for each focused sample data set.

The reliability evaluator 102f evaluates reliability of the focused sample data set based on at least one reliability evaluation index (the sample reliability evaluation index and an average value thereof) calculated by the reliability evaluation index calculator 102e for each sample data set and stores data related to an evaluation result thereof in a predetermined storage area of the evaluation result data file 106c.

The result output unit 102g outputs the reliability evaluation index calculated by the reliability evaluation index calculator 102e and evaluation results by the reliability evaluator 102f to the output device 112.

An external system 200 is communicatably connected to the sample data reliability evaluation apparatus 100 thorough the network 300, is provided with an external database about a sample data set and the like, and has function of providing external program for executing various processing, and the like. The external system 200 can be configured as WEB server, ASP server, and the like, and the hardware can be configured by an information processing device and the accessory devices such as existing personal computer, and workstation. Each function of the external system 200 can be realized by CPU in the external system 200, a disk device, a memory device, the input device, the output device, a communication control device, and the like, and a computer program etc. controlling these devices.

The network 300 has function of connecting the sample data reliability evaluation apparatus 100 with the external system 200, and may at least include internet, intranet, LAN (wired/wireless), VAN, personal computer communication network, public telephone network (analog/digital), leased circuit (analog/digital), cable TV network, mobile phone switching network/packet-switching data network by IMT2000, GSM, PDC/PDC-P, or the like, radio paging network, local wireless network such as Bluetooth®, PHS network, satellite communication network such as CS, BS, and ISDB, and the like. The sample data reliability evaluation apparatus 100 can transmit and receive various data through any wired or wireless network.

Processing of the System

Figure 5:
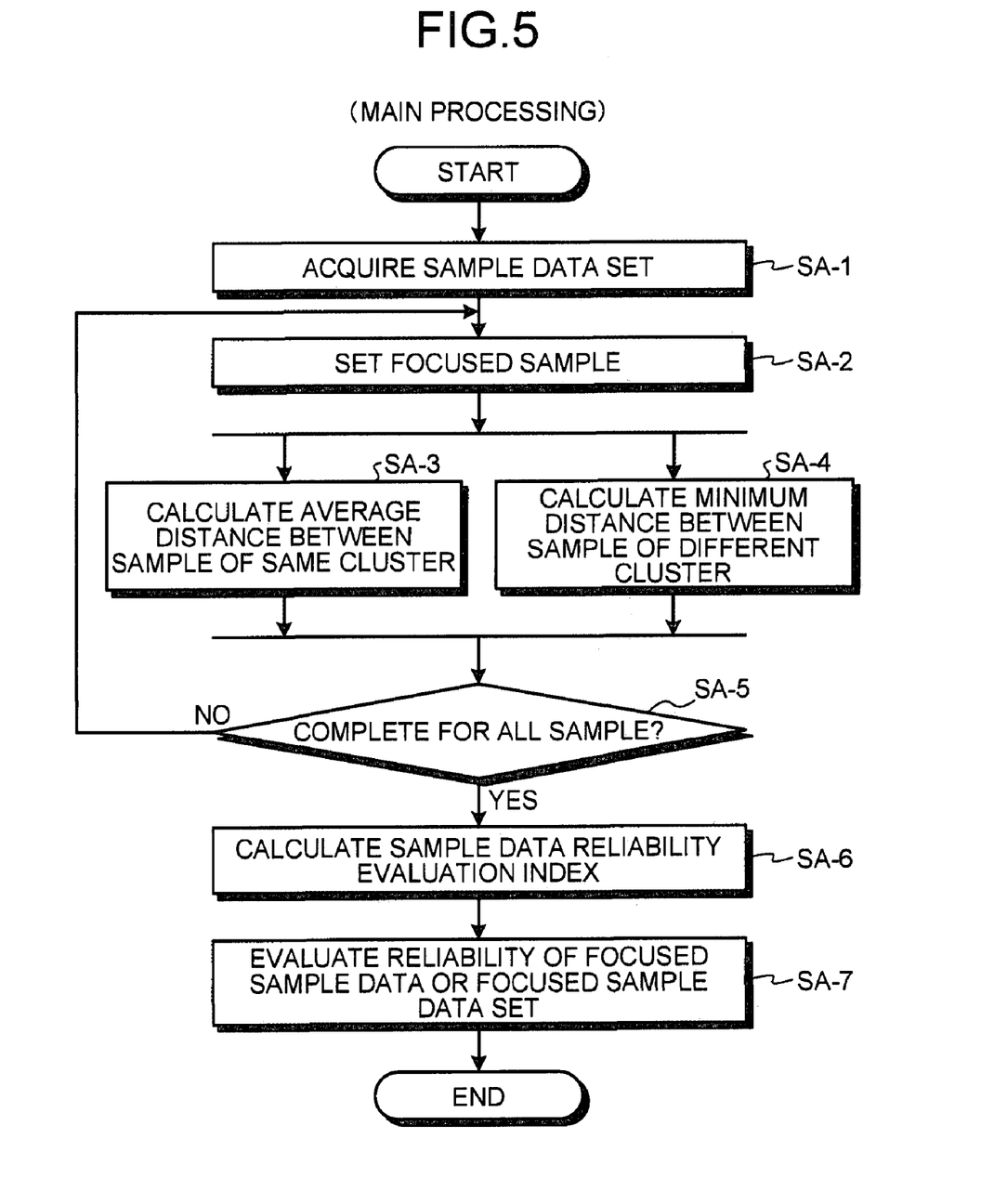
FIG. 5 is a flow chart exemplifying main processing performed by a control unit 102 of the sample data reliability evaluation apparatus 100.

The following describes in detail one example of the main processing executed by the control unit 102 of the sample data reliability evaluation apparatus 100 with reference to FIG. 5. FIG. 5 is a flow chart exemplifying main processing performed by the control unit 102 of the sample data reliability evaluation apparatus 100. Here, processing based on a sample data set corresponding to one experiment will be described.

First, the control unit 102 acquires a sample data set by processing of the sample data set acquirer 102*a* from the external system 200 via the network 300 and stores the acquired sample data set in the predetermined storage area of the sample data set file 106*a* (step SA-1).

Next, the control unit 102 sets a focused sample from among the sample data set acquired at step SA-1 by processing of the focused sample setter 102*b* (step SA-2).

Next, the control unit 102 calculates an average distance between samples of the same cluster corresponding to the focused sample set at step SA-2 based on the sample data set stored in the sample data set file 106*a* by processing of the representative distance calculator between sample of same cluster 102*c* and stores the calculated average distance between samples of the same cluster in the predetermined storage area of the focused sample related data file 106*b* (step SA-3).

Here, the average distance between samples of the same cluster may be calculated based on the formula 1 shown below at step SA-3.

[Eq. 1]

$$d_1 = \frac{\sum_{j=1, j \neq i}^{n} \sqrt{(a_i - a_j)^2 + (b_i - b_j)^2}}{n} \quad \text{(FORMULA 1)}$$

In the formula 1, $d_1$ is the average distance between samples of the same cluster, $(a_i, b_i)$ is signal data of a focused sample i itself, $(a_j, b_j)$ is signal data contained in sample data corresponding to a sample belonging to the same cluster as the focused sample, n is the total number of samples contained in the cluster to which the focused sample belongs. $d_1$ changes depending on the sample, even if the sample belongs to the same cluster.

In parallel with step SA-3, the control unit 102 also calculates a minimum distance between samples of different clusters corresponding to the focused sample set at step SA-2 based on the sample data set stored in the sample data set file 106*a* by processing of the representative distance calculator between sample of different cluster 102*d* and stores the calculated minimum distance between samples of different clusters in the predetermined storage area of the focused sample related data file 106*b* (step SA-4).

Here, the minimum distance between samples of different clusters may be calculated based on the formula 2 shown below at step SA-4.

[Eq. 2]

$$d_2 = \min[\sqrt{(a_i - a_k)^2 + (b_i - b_k)^2}] \quad \text{(FORMULA 2)}$$

In the formula 2, $d_2$ is the minimum distance between samples of different clusters, $(a_i, b_i)$ is signal data of a focused sample i itself, and $(a_k, b_k)$ is signal data contained in sample data corresponding to a sample belonging to a different cluster from that to which the focused sample belongs. $d_2$ changes depending on the sample, even if the sample belongs to the same cluster.

Next, the control unit 102 checks whether or not step SA-2 to step SA-4 have been completed for all samples in the sample data set stored in the sample data set file 106*a*. If the check result is not "completed" (step SA-5: No), the control unit 102 causes each processing unit to perform step SA-2 to step SA-4 and if the check result is "completed" (step SA-5: Yes), the control unit 102 causes the reliability evaluation index calculator 102*e* to perform step SA-6 described later.

Next, the control unit 102 calculates a ratio of the average distance between samples of the same cluster to the minimum distance between samples of different clusters as the sample reliability evaluation index based on a pair of each focused sample of the average distance between samples of the same cluster calculated at step SA-3 and the minimum distance between samples of different clusters calculated at step SA-4 by processing of the reliability evaluation index calculator 102*e* for each piece of focused sample data, stores a plurality of calculated sample reliability evaluation indexes in the predetermined storage area of the focused sample related data file 106*b*, and calculates an average value of the plurality of calculated sample reliability evaluation indexes (step SA-6).

Here, the sample data reliability evaluation index may be calculated based on the formula 3 shown below at step SA-6.

[Eq. 3]

$$QV = d_1/d_2 \quad \text{(FORMULA 3)}$$

In the formula 3, QV is the sample data reliability evaluation index in a focused sample i, $d_1$ is the average distance between samples of the same cluster shown in the formula 1, and $d_2$ is the minimum distance between samples of different clusters shown in the formula 2.

Next, the control unit 102 evaluates reliability of focused sample data based on the plurality of sample reliability evaluation indexes calculated at step SA-6 by processing of the reliability evaluator 102*f* for each piece of focused sample data and also evaluates reliability of the focused sample data set based on an average value of the plurality of sample reliability evaluation indexes calculated at step SA-6 for each focused sample data set to store data related to these evaluation results in the predetermined storage area of the evaluation result data file 106*c* (step SA-7).

One example of the main processing executed by the control unit 102 of the sample data reliability evaluation apparatus 100 is terminated.

SUMMARY OF THE PRESENT EMBODIMENT AND OTHER EMBODIMENTS

According to the present embodiment, as described above, a sample data set is acquired, a focused sample is set from among the sample data set, an average distance between samples of the same cluster and a minimum distance between samples of different clusters are calculated for the set focused sample, and focused sample settings and calculation of the average distance between samples of the same cluster and minimum distance between samples of different clusters are repeatedly performed for all samples in the sample data set to calculate a ratio of the average distance between samples of the same cluster to the minimum distance between samples of different clusters as the sample reliability evaluation index based on a pair of each focused sample of the calculated average distance between samples of the same cluster and minimum distance between samples of different clusters for each piece of focused sample data and also an average value of sample reliability evaluation indexes is calculated for each focused sample data set to evaluate reliability of the focused sample data based on a plurality of calculated sample data reliability evaluation indexes for each piece of focused sample data and to evaluate reliability of the focused sample data set based on a plurality of calculated average values for each focused sample data set. The reliability of polymorphic data can be objectively evaluated, particularly even if polymorphic data containing polymorphism whose frequency is small is obtained from polymorphic analysis concerning genetic polymorphism. Here, in the present embodiment, as an example, the average distance between samples of the same cluster is calculated based on the formula 1 as a representative distance, but the representative distance may be calculated, in addition to the average distance, as a median, a mode, or an average value by excluding the maximum and minimum values, or an average value may be newly calculated by excluding data that is apart from the average value by twice the variance or more.

According to the embodiment, the focused sample data set may have one piece of sample data as an element, a plurality of pieces of sample data as elements, or all pieces of sample data as elements. Accordingly, the reliability evaluation index can be calculated in units of samples, clusters, or total samples (specifically, in units of experiment); as a result, an effect of being able to evaluate reliability of a sample data subset in units of samples, clusters, or total samples (specifically, in units of experiment) is obtained.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth. For example, the sample data reliability evaluation apparatus 100 can be configured to perform processes in response to request from a client terminal, which is a separate unit, and return the process results to the client terminal. All the automatic processes explained in the present embodiment can be, entirely or partially, carried out manually. Similarly, all the manual processes explained in the present embodiment can be, entirely or partially, carried out automatically by a known method. The process procedures, the control procedures, specific names, information including registration data for each process and various parameters such as search conditions, display example, and database construction, mentioned in the description and drawings can be changed as required unless otherwise specified.

The constituent elements of the sample data reliability evaluation apparatus 100 are merely conceptual and may not necessarily physically resemble the structures shown in the drawings. For instance, the apparatus need not necessarily have the structure that is illustrated. For example, the process functions performed by each device of the sample data reliability evaluation apparatus 100, especially the each process function performed by the control unit 102, can be entirely or partially realized by CPU and a computer program executed by the CPU or by a hardware using wired logic. The computer program, recorded on a recording medium to be described later, can be mechanically read by the sample data reliability evaluation apparatus 100 as the situation demands. In other words, the storage unit 106 such as ROM or HD stores the computer program that can work in coordination with OS to issue commands to the CPU and cause the CPU to perform various processes. The computer program is first loaded to RAM, and forms the control unit 102 in collaboration with the CPU. Alternatively, the computer program can be stored in any application program server connected to the sample data reliability evaluation apparatus 100 via the network 300, and can be fully or partially loaded as the situation demands.

The computer-readable recording medium on which the computer program can be stored may be a portable type such as flexible disk, magneto optic (MO) disk, ROM, erasable programmable ROM (EPROM), electrically erasable programmable ROM (EEPROM), compact disk-read-only memory (CD-ROM), digital versatile disk (DVD), or a communication medium that stores the computer program for a short term such as communication channels or carrier waves that transmit the computer program over the network 300 such as LAN, wide area network (WAN), and the Internet. Computer program refers to a data processing method written in any computer language and written method, and can have software codes and binary codes in any format. The computer program can be a dispersed form in the form of a plurality of modules or libraries, or can perform various functions in collaboration with a different program such as the OS. Any known configuration in the each device according to the embodiment can be used for reading the recording medium. Similarly, any known process procedure for reading or installing the computer program can be used.

The sample data reliability evaluation apparatus 100 can also be connected to any existing personal computer, workstation, etc. and can be operated by executing software (that includes computer program, data, etc.) that implements the method according to the present invention in the personal computer or workstation.

The distribution and integration of the sample data reliability evaluation apparatus 100 are not limited to those illustrated in the figures. The device as a whole or in parts can be functionally or physically distributed or integrated in an arbitrary unit according to various attachments or how the device is to be used. For example, each database may form a stand-alone database device, and a part of process may be executed by using common gateway interface (CGI).

EXAMPLE

Here, a specific example of the reliability evaluation index (more specifically, QV according to the above embodiment or an average value ($QV_{avg.}$) of QV) calculated by the sample data reliability evaluation apparatus 100 according to the above embodiment.

First, monobasic polymorphism of a human being is typed by SSPCE-FCS (See "Current Pharmaceutical Biotechnology, 2003, 4, 447-484"), signals corresponding to each Allele in each sample are measured by a unimolecular fluorometer (MF10S, manufactured by Olympus), and measurement results thereof were clustered by type. Then, signal data of clustered samples was selected as input data of the sample data reliability evaluation apparatus 100.

Figure 6:
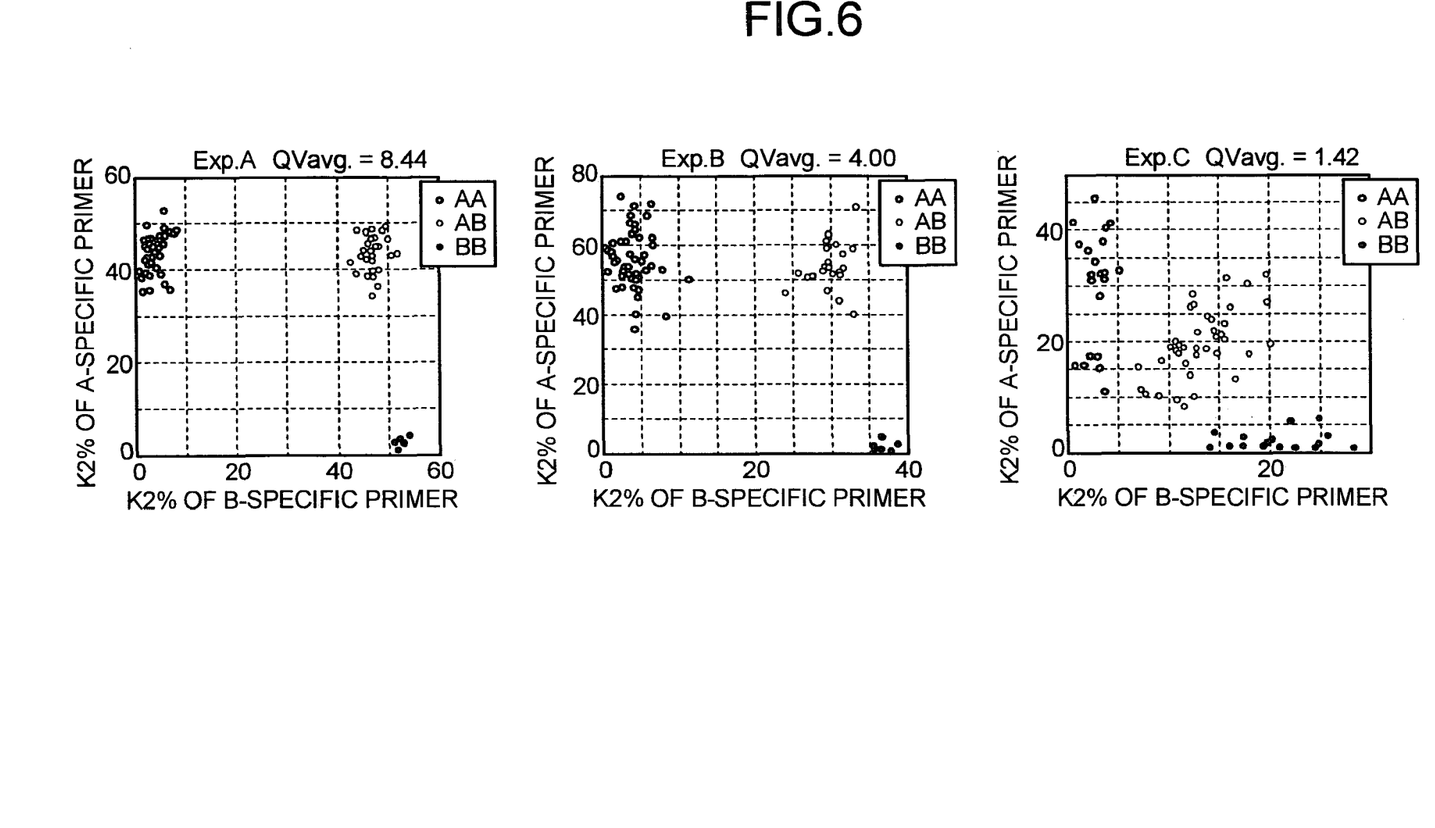
FIG. 6 is a diagram exemplifying $QV_{avg.}$ calculated for each experiment unit.

FIG. 6 shows the reliability evaluation index ($QV_{avg.}$) calculated for each experiment. The $QV_{avg.}$ is an average value of 80 QV calculated for each sample of 80 samples contained in the experiment carried out in a 96-well plate. As shown in FIG. 6, clustering conditions become worse in the order of Experiment A (Exp. A), Experiment B (Exp. B), and Experiment C (Exp. C). Then, with worsening clustering conditions, the value of $QV_{avg.}$ becomes worse like 8.44, 4.00, and 1.42. Thus, the value of $QV_{avg.}$ corresponds to changes of clustering conditions in units of experiment.

Figure 7:
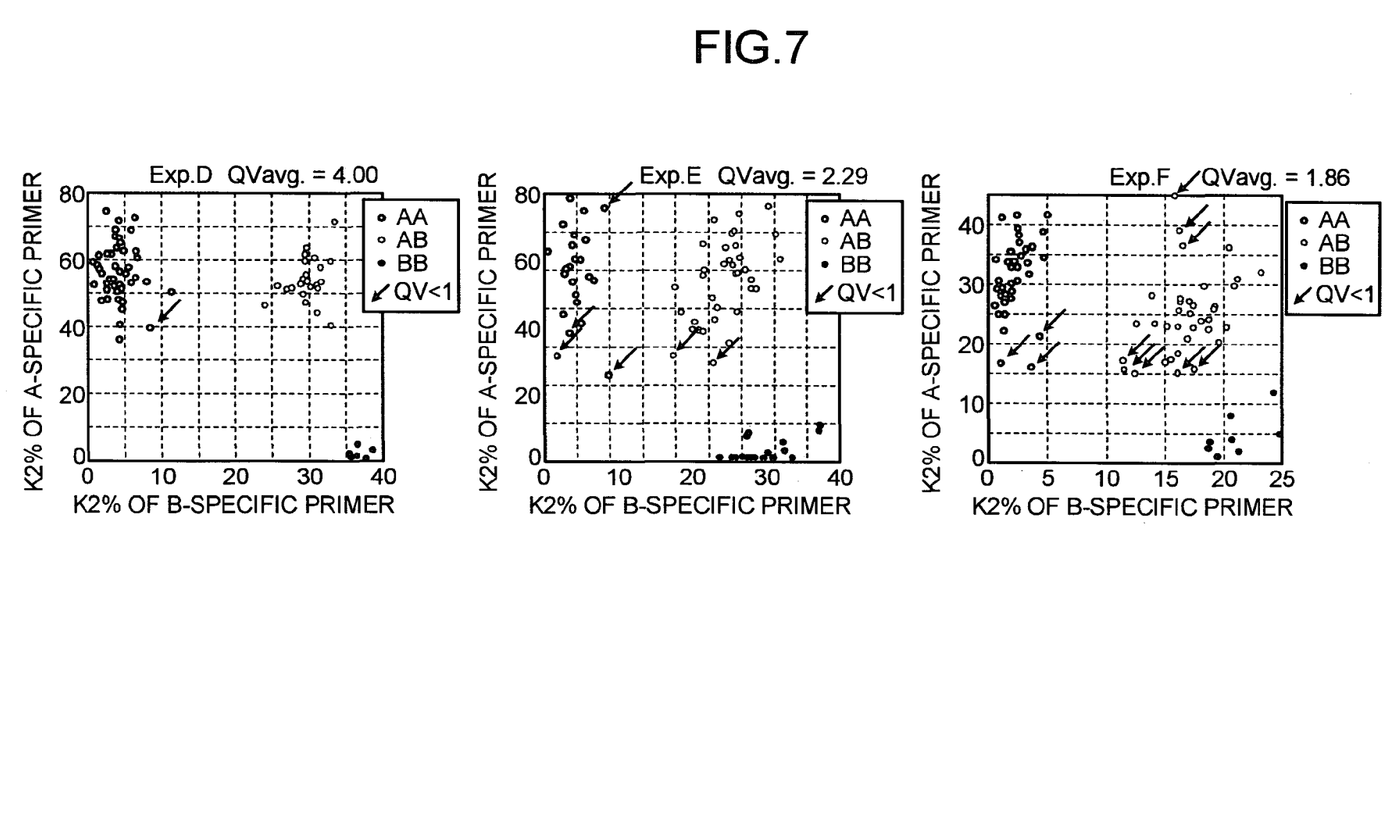
FIG. 7 is a diagram exemplifying error sample extraction.

Next, extraction of poorly separated samples (poorly typed samples, error samples) was attempted using the reliability evaluation index (QV) obtained for each sample. FIG. 7 shows results thereof. In FIG. 7, an arrow is attached to samples whose value of QV falls short of 1. QV falling short of 1 means that the average distance to the same type becomes larger than that to the nearest of other types. Then, as shown in FIG. 7, samples having QV falling short of 1 are concentrated in border areas of clusters. This allowed us to extract samples of ambiguous separation based on the value of QV.

Figure 8:
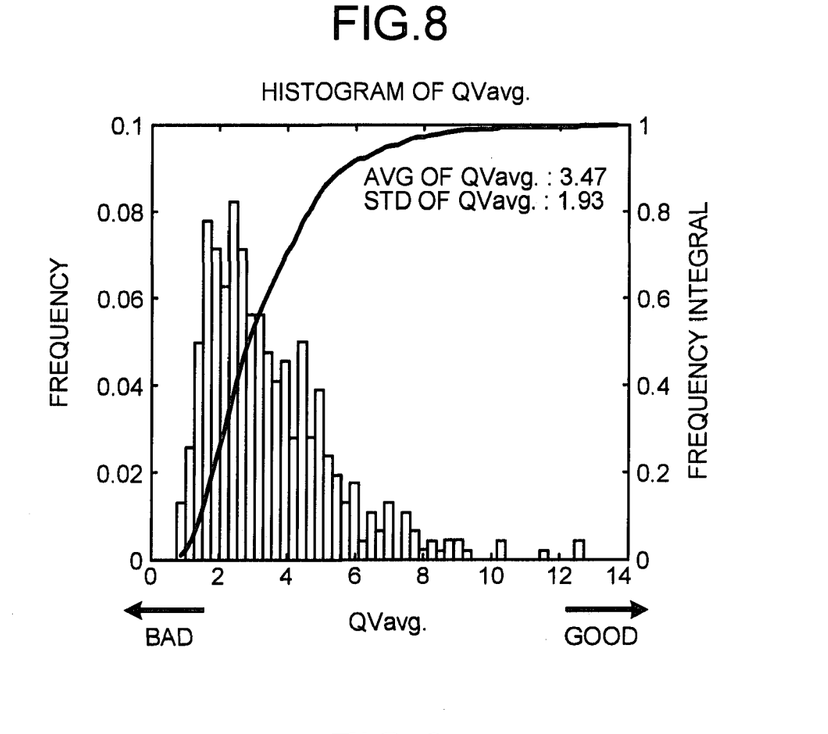
FIG. 8 is a diagram exemplifying a histogram of $QV_{avg.}$.

Next, FIG. 8 shows a histogram of about 600 $QV_{avg.}$ calculated for each experiment of about 600 experiments (One experiment consists of 80 samples). Since QV is correlated with separation conditions, quality of input data can be clarified by comparing $QV_{avg.}$ among experiments.

Figure 9:
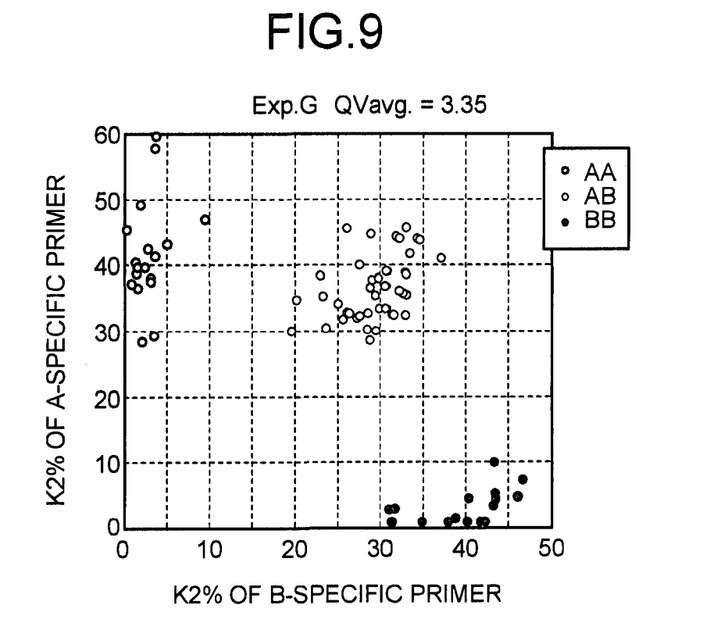
FIG. 9 is a diagram showing $QV_{avg.}$ corresponding to an experiment having average input data quality in FIG. 8.

By showing $QV_{avg.}$ calculated for each experiment in a histogram, quality of input data corresponding to the experiment currently focused can objectively be compared with that of other experiments. FIG. 9 is a diagram showing $QV_{avg.}$ corresponding to an experiment having average input data quality in FIG. 8. The average value of $QV_{avg.}$ in the whole experiments of about 600 is 3.47 and FIG. 9 shows a scatter diagram of Experiment G corresponding to 3.35 of $QV_{avg.}$, which is near the average value.

The foregoing shows that QV and $QV_{avg.}$ are useful as indexes for evaluating reliability of typing results. Also, by using the histogram of $QV_{avg.}$ shown in FIG. 8, reliability of a plurality of experiments can be shown to third parties objectively. In addition, automatic extraction of error samples can be realized by QV. Accordingly, the sample data reliability evaluation method executed by the sample data reliability evaluation apparatus 100 can be used as an automatic extraction algorithm of error samples.

The present invention includes a first calculating step of calculating a representative distance between samples of a same cluster, which is a representative distance between the sample and the sample belonging to the same cluster to that to which the sample belongs, based on a sample data set having a plurality of pieces of sample data concerning clustered samples as elements, a second calculating step of calculating a representative distance between samples of different clusters, which is a representative distance between the sample and the sample belonging to the different cluster from that to which the sample belongs based on the sample data set, a third calculating step of calculating a reliability evaluation index, which is an index for evaluating reliability of the sample data based on the representative distance between samples of the same cluster calculated at the first calculating step and the representative distance between samples of different clusters calculated at the second calculating step, and an evaluating step of evaluating the reliability of a subset of the sample data set or the whole sample data set based on the reliability evaluation index calculated at the third calculating step. Therefore, particularly even if polymorphic data containing polymorphism whose frequency is small is obtained from polymorphic analysis concerning genetic polymorphism, an effect of being able to objectively evaluate such polymorphic data is achieved.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A sample data reliability evaluation method comprising:
a first calculating step of calculating a representative distance between samples of a same cluster, which is a representative distance between one sample and at least one other sample, the one sample and the at least one other sample belonging to the same cluster, based on a sample data set having a plurality of pieces of sample data concerning clustered samples as elements;
a second calculating step of calculating a representative distance between samples of different clusters, which is a representative distance between the one sample and at least one different sample, the at least one different sample belonging to a different cluster from the cluster of the one sample, based on the sample data set;
a third calculating step of calculating a reliability evaluation index, which is an index for evaluating reliability of the sample data based on the representative distance between samples of the same cluster calculated at the first calculating step and the representative distance between samples of different clusters calculated at the second calculating step; and
an evaluating step of evaluating the reliability of a subset of the sample data set or a whole of the sample data set based on the reliability evaluation index calculated at the third calculating step.

2. The sample data reliability evaluation method according to claim 1, wherein
the representative distance between samples of the same cluster is an average distance between the one sample and the at least one other sample, the one sample and the at least one other sample belonging to the same cluster,
the representative distance between samples of different clusters is a minimum distance between the one sample and the at least one different sample, the at least one different sample belonging to the different cluster from the cluster of the one sample, and
the reliability evaluation index is a ratio of the representative distance between samples of the same cluster to the representative distance between samples of different clusters or an average value of the ratio.

3. The sample data reliability evaluation method according to claim 1 or 2, wherein
the evaluation of the reliability of the subset of the sample data set or the whole of the sample data set is extraction of the subset of the sample data set or the whole of the sample data set with the low reliability or the evaluation of reliability of an algorithm used for the clustering.

4. The sample data reliability evaluation method according to claim 1, further comprising:
an outputting step of outputting the reliability evaluation index calculated at the third calculating step.

5. A sample data reliability evaluation apparatus comprising:
a first calculator that calculates a representative distance between samples of a same cluster, which is a representative distance between one sample and at least one other sample, the one sample and the at least one other sample belonging to the same cluster, based on a sample data set having a plurality of pieces of sample data concerning clustered samples as elements;
a second calculator that calculates a representative distance between samples of different clusters, which is a representative distance between the one sample and at least one different sample, the at least one different sample belonging to a different cluster from the cluster of the one sample, based on the sample data set;
a third calculator that calculates a reliability evaluation index, which is an index for evaluating reliability of the sample data based on the representative distance between samples of the same cluster calculated by the first calculator and the representative distance between samples of different clusters calculated by the second calculator; and an evaluator that evaluates the reliability of a subset of the sample data set or a whole of the sample data set based on the reliability evaluation index calculated by the third calculator.

6. The sample data reliability evaluation apparatus according to claim 5, wherein
the representative distance between samples of the same cluster is an average distance between the one sample and the at least one other sample, the one sample and the at least one other sample belonging to the same cluster,
the representative distance between samples of different clusters is a minimum distance between the one sample and the at least one different sample, the at least one different sample belonging to the different cluster from the cluster of the one sample, and
the reliability evaluation index is a ratio of the representative distance between samples of the same cluster to the representative distance between samples of different clusters or an average value of the ratio.

7. The sample data reliability evaluation apparatus according to claim 5 or 6, wherein
the evaluation of the reliability of the subset of the sample data set or the whole of the sample data set is extraction of the subset of the sample data set or the whole of the sample data set with the low reliability or the evaluation of reliability of an algorithm used for the clustering.

8. The sample data reliability evaluation apparatus according to claim 5, further comprising:
an output unit that outputs the reliability evaluation index calculated by the third calculator.

\* \* \* \* \*